United States Patent [19]
Bax

[11] Patent Number: 4,957,438
[45] Date of Patent: Sep. 18, 1990

[54] DENTAL COUPLING ASSEMBLY AND METHOD FOR ITS USE

[75] Inventor: Arthur Bax, Schilde, Belgium

[73] Assignee: CEKA N.V., Antwerpen, Belgium

[21] Appl. No.: 236,360

[22] PCT Filed: Nov. 25, 1987

[86] PCT No.: PCT/DE87/00547
 § 371 Date: Jul. 12, 1988
 § 102(e) Date: Jul. 12, 1988

[87] PCT Pub. No.: WO88/03786
 PCT Pub. Date: Jun. 2, 1988

[30] Foreign Application Priority Data
Nov. 25, 1986 [DE] Fed. Rep. of Germany ........ 3640163
Mar. 9, 1987 [DE] Fed. Rep. of Germany ........ 3707483
Nov. 23, 1987 [DE] Fed. Rep. of Germany ........ 3739646

[51] Int. Cl.⁵ .................................... A61C 13/225
[52] U.S. Cl. ..................................... 433/180; 433/177; 433/181; 433/189; 433/192
[58] Field of Search ............... 433/169, 167, 172, 173, 433/174, 175, 176, 180, 181, 182, 191, 192, 219, 189, 177

[56] References Cited

U.S. PATENT DOCUMENTS

| 4,530,663 | 7/1985 | Pornoy | 433/189 |
| 4,711,631 | 12/1987 | Thomson | 433/181 |

FOREIGN PATENT DOCUMENTS

| 2952561 | 7/1981 | Fed. Rep. of Germany | 433/172 |
| 8531967 | 3/1986 | Fed. Rep. of Germany | |

Primary Examiner—Cary E. Stone
Attorney, Agent, or Firm—Herbert Dubno

[57] ABSTRACT

A dental coupling assembly for anchoring a prosthesis in the mouth in which a holding member has a recess defined by a straight right circular cylindrical wall and a closed bottom which confronts the outer right circular cylindrical wall of a plug member whose end receivable within the recess is likewise closed so that the plug member forms a displacement body for displacing a fluid adhesive throughout the cylindrical gap between the two members and between the bottom wall of the recess and the end surface of the plug. Because the walls are cylindrical and not undercut or tapered, the parts can be machined with greater precision and ease while allowing adjustment because of the adhesive field gap. The T-shaped slots and other lateral openings need not be provided.

10 Claims, 6 Drawing Sheets

DENTAL COUPLING ASSEMBLY AND METHOD FOR ITS USE

CROSS REFERENCE TO RELATED APPLICATION

This application is a national phase of PCT/DE87/00547 filed 25 Nov. 1987 and based, under the International applications P 36 40 163.3 filed 25 Nov. 1986, P 37 07 483.2 filed 9 Mar. 1987 and P 37 39 646.3 filed 23 Nov. 1987.

FIELD OF THE INVENTION

The invention relates to a dental coupling assembly and method of applying same. A prior art dental coupling assembly is known from German Patent 35 25 298. Another dental coupling assembly is known from the German open application 34 32 486. A common feature of this state of the art is that the coupling assembly serves for a connection—which is first loose but can be locked in position with a hardenable mass—between a dental prosthetic structure and one of the two parts —male or female—of a dental attachment or of an anchoring device. Thereby, an insertion—or retention part is provided with outer shell surfaces and is insertable into a hollow holding recess with play and is movable within the holding recess with the tolerances desirable for the attachment—and prosthesis-ancharing techniques, prior to the introduction of a hardenable mass. The outer shell surface of the retention part has at least two partial outer shell surfaces, which are inclined with respect to the median axis of the recess and parallel with respect to the partial inner-shell surfaces of the recess.

OBJECT OF THE INVENTION

While the known coupling assembly (German Patent 35 25 298) has performed well in practice, the invention has and its object to improve the known dental coupling assembly in such manner that can be possible in any case to produced with less effort and that, in will facilitate the work done in the patient's mouth for its insertion.

SUMMARY OF THE INVENTION

This object is achieved by providing a dental coupling assembly with a brace attachable in the mouth of the patient to which a metal holding part optionally formed by a model of synthetic material burning off without residue, is fastened or can be fastened, having a recess with a continuously closed inner shell surface, and wherein a retention part is held with the aid of an adhesive, particularly a hardening cement, whereby the recess is enlarged in comparison to the outer volume of the retention part by a space affording free play to the retention part, and with a complementary coupling part provided with a dental-prosthesis structure, which engages with the retention part with at least one detachable coupling connection. According to the invention, the recess and retention part have over the entire extent of their axial length the inner wall surface or the outer wall surface of a straight (right) circular cylinder. The recess is closed at its one inner frontal side with an inner bottom surface and the retention part is closed by an outer bottom surface facing the inner bottom surface.

Thus, the recess and the retention part each represent over the entire axial extent an inner shell or wall surface and the outer shell or wall surface of a straight (right) circular cylinder. In addition, the recess is closed by an inner bottom surface at one of its inner frontal ends, while the retention part is closed by an outer bottom surface facing the inner bottom surface.

The recess according to the invention, wherein the retention part to be cemented is received with spatial play, is, for instance during repair in the patient's mouth, particlualrly easy to make, with a cylindrical instrument (cylindrical cutter or ther like). Such a straight circular-cylindrical recess in the case of a holder model burnable without residues, can be made as a plastic part through die casting, which is easily extracted from the mold from the point of view of the tools.

Surprising in the case of the coupling assembly of the invention is the fact that with a recess that is not undercut (compared to German Patent 35 25 298 and German open specification 34 32 486), it is possible to raise the required thrust force for the locking between the retention part and the complementary coupling part (e.g. female part and snap-button-like male part). This surprising result apparently can be explained by the fact that due to the precise alignment adjusting possibilities between the retention part and the complementary coupling part, damaging can be avoided. In this way, the cement connection between the retention part and the recess can be made so that with some additional measure for safety, it will have to absorb only the arresting force within the detachable coupling connection, i.e. practically only the pure axial-force component. This pure axial-force component in the case of an eye-like female part and a therein lockable snap-button like make part made of spring segments can be for instance of the order of 0.8 daN.

It is also a feature of the invention that the recess as well as the retention part are provided with surrounding shell surfaces (inner shell surface and outer shell surface) and with bottom surfaces sealingly fastened thereto. In this way, the retention part can act during its insertion as a displacement body upon the cement previously introduced into the recess, distributing it evenly over the inner shell surface of the recess and the outer shell surface of the retention part. In comparison thereto, the walling of the holding recess in the German open specification 34 32 486 is axially slitted, thus not being sealed off, while the holding recess of German Patent 35 25 298 has no bottom surface.

According to the invention the inner bottom surface of the recess is a flat circular surface. The inner bottom surface of the recess can have, alternatively, the shape of a concave calotte.

Advantageously the inner bottom surface and the inner shell surface of the recess are connected to each other over a concavely arched circular annular surface.

The outer bottom surface of the retention part can be a straight circular surface or can have the shape of a convex calotte. Here too, the outer bottom surface and the outer shell surface of the retention part can be connected to each other over a convexly arched circular annular surface.

The retention part can be a pot-shaped eyelet-like female part with an undercut central hollow space for a complementary coupling part which is an anchor-like male part. The outer bottom surface of the pot-shaped eyelet can consist of a bottom made in one piece and of the same material as the eyelet particularly representing a rotating part. The retention can be a pot-shaped internally threaded bushing.

The retention part can be a magnet or ferromagnetic component for a complementary coupling part, which is a ferromagnetic component or a magnet, respectively.

The recess can be provided extracoronally on the holding part of a post tooth and intracoronally on a holding part of the root. The recess can also be arranged in a connection bridge representing the holding part. The recess can as well be provided at the free frontal side of an implant forming the holding part.

Corresponding to the German Utility Model 85 18 324 (see there page 5, par. 2) a retention part, namely an eye-like female part, whose outer shell surface is smooth and circularly-cylindrical over the entire axial length, is cemented into a correlated hollow of a prosthesis part made of steel.

Corresponding to a further embodiment of the German Utility Model 85 18 824, an externally waisted eyelet is surrounded on the outside by a sprayed ring of synthetic material, having a smooth circular-cylindrical outer shell surface. The ring of synthetic material can be burned without residue (see German Utility Model 85 18 324, page 6 par. 2) and therefore is suited to be received with a clamp- or pressfit in an equally smooth circular-cylindrical recess of a model made of synthetic material, which can also be burned off without leaving residues. This model of synthetic material is first connected to the wax model of a post tooth of the master model, and then cast in metal together with the post crown, as a holding part by the lost-wax method. Due to the fact that the synthetic material ring burns off without residue, the eyelet is extracoronally integrally cast with the metal holdign part. The parts according to the German Utility Model 85 18 324 require a very precise tolerance-free doubling work, in order to avoid deviations the parallelism. Particularly the anchoring devices shown in the German Utility Model 85 18 324 and in the German Patent 35 25 298 require a parallelism with minimum tolerance, since the median axes of the eyelet and the anchor of the male part have to coincide, thus practically not allowing any deviation from parallelism.

The invention improves on the object to further improve on the known method by using the coupling assembly of the invention in such a way as to make it possible that the retention part can be fastened in the recess of a metal holding part in a simpler way or at least in the same way as before, but with less preparatory precision work. In the method of the invention the recess is provided with a receiving volume, which, with respect to the space requirement of the retention part, is enlarged by a free-play space for the retention part. Thereafter the shell-side and/or bottom-side finishing area of the retention part and/or the recess are provided with a hardenable cement, the retention part is inserted into the recess while being held parallely to itself, aligned and there held in the aligned position until the cement has hardened.

The method according to the invention creates the possibility to counteract the tolerances resulting from the doubling technique during the manufacture of prosthesis arrangements. At the same time, with this method it is possible for the retention part, e.g. an eyelet-like female part which is at first movably arranged in the still soft cement bed of the holding recess, to be after thereafter adjusted with a very precise fit in the recess. Such a precise adjustment is particularly important in the case of the snap-button type couplings, where the mutual engagement of the parts-as mentioned-allows only very narrow tolerances, these couplings consisting of a femal part eyelet and of a coaxially engaging male part anchor. First of all, it is essential that the method be performed with the simplest possible means, since a right circular-cylindrical pot-shaped hollow is easily made with a spatial surplus, without considering tolerances worth mentioning.

From the German open specification 34 32 486 (compare there FIG. 9 in connection with page 19, last paragarph, as well as page 20, par. 1) a device for the connection of a model cast structure as part of a removable prosthesis with the its anchor can be seen. The concept "anchor" is not accurate in this case, since only a telescopic crown is shown as an "anchor", which, considering its special function, cna not at all be compared with the features of the generic snap-button anchor. The know connection arrangement provided in order to balance the tolerances is connected on one side to the crown and on the other side with the model structure. The connection arrangement between the model structure and the crown consists of a female hollow part, wherein a male connection part is first movably received, and than after adjustment, is permanently arrested in a very precisely established position with a filler. Thus, in the device of the German open specification 34 32 486, the positions of the individual elements of the telescopic crown -which can not be compared at all to a snap-button anchor—are not influenced. In contradistinction, with the method of the ivention, the mobility of the arrangement prior to the hardening of the cement is used in the case of the otherwise very hard to adjust known retention part (for instance an eyelet-like female part) in order to establish from the start a precisely aligned arrangement between the retention part and the complementary coupling part.

German open specification 85 18 324 describes a method whereby first a holding part made of residue-free burnable synthetic material is connected to the wax model of the post tooth of a master model and then, through the lost-wax technique, a post crown is cast in metal with the holding part and the retention part is received and fastened in the metal holding part. In accordance with the invention, this known method is further improved, so that at first the recess arranged in the optionally pot-shaped plastic holding part is formed with a receiving volume increased by the space required for the play of the retention part in the metal holding part, after which the retention part is set with a parallel pin in the recess provided with a hardenable cement and is held together with the parallel pin in the adjusted position until the hardening is completed. The method according to the invention enables the tolerances created during doubling, which influence the position in space of the metal holding part produced during casting, to be completely eliminated with respect to the precise mutual position of the two elements of the snap button.

This is the case because the inserting position of the retention part is not transmitted through the doubling process, possibly with tolerances, but rather is finally defined in the last stages.

The invention is also applicable to repair in the moouth of the patient, whereby an existing used retention part, e.g. an eyelet-like female part, has to be replaced with a new one. After removal, removal or by drilling out, of the worn retention part, it is sufficient to widen the recess and after that to build in the eyelet, according to the method characteristics defined in patent.

The method of the invention can also be analogously applied to extracoronal and intracoronal (axial) arrangements. Besides the recess can be provided in a connection bridge forming the holding part or in the free frontal side of an implant forming the holding part or of an implant insertion. The recess can receive alternatively a pot-shaped eyelet, a pot-shaped internally-threaded bushing, a circular-cylindrical magnet, or a corresponding ferromagnetic part.

BRIEF DESCRIPTION OF THE DRAWING

The above and other objects, features and advantages of my invention will become more readily apparent from the following description, reference being made to the accompanying highly diagrammatic drawing in which.

SPECIFIC DESCRIPTION

Figure 1:
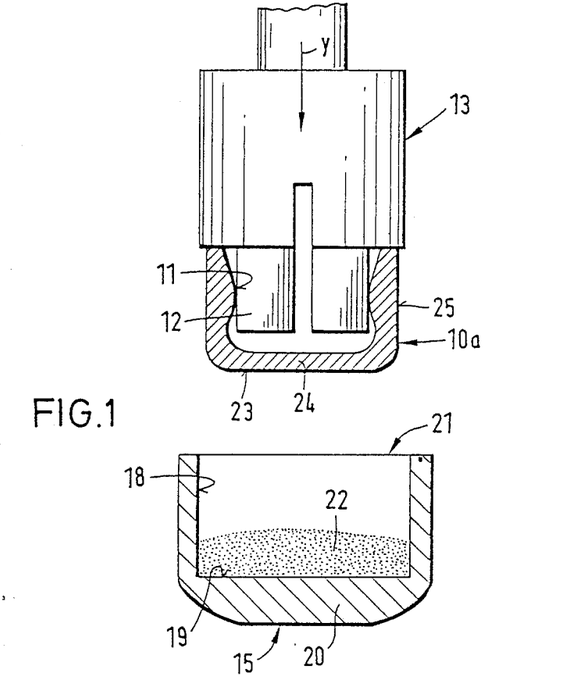
FIG. 1 and 2 are sectional views which illustrate the method for the insertion of a pot-shaped female eyelet part.

At the top of FIG. 1, a female eyelet-like part 10a having an inner retention surface 11 for the snap-button-like engagement with a male anchor-like part 26 (see FIG. 3) is illustrated. In the present case, eyelet 10a and anchor 26 correspond basically for instance with the arrangements shown in German Utility Model 85 18 324 (FIG. 1 and 2).

The eyelet 10a is received in an adjusted position by the inner braceable clamping jaws 12 of a parallel holder, or parallel pin 13.

Also adjusted in position is a metal holding part 15, whose basic construction can also be seen from German Utility Model 85 18 324 (see there FIG. 3). The metal holding part 15 is fastened to a post crown (not shown) by means not shown in the drawing, such as for instance a bracket 16 made in one piece therewith and a fastening plate 17 (see FIG. 4 and 5).

The holding piece 15 is provided with a holding arrangement 21 open towards the parallel pin 13, which is limited by the inner shell surface 18 (here the inner wall of a right circular cylinder) and by the circular bottom surface 19. The bottom 20 of the metal holding part 15 is therefore closed.

In the hollow recess 21 is a certain amount of fluid cement 22, which suitably has a short pot time, i.e. is quick-hardening.

The outer bottom surface 23 of the eyelet-like female part is continuous i.e. the eyelet is closed by a bottom 24. The eyelet 10a represents a one-piece rotating part.

Figure 2:
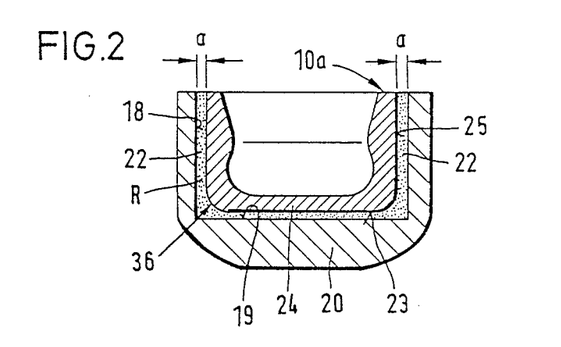

The parallel pin 13 carrying the eyelet 10a is now introduced in to the direction y towards the holding part 15 and inserted in the recess 21 until the eyelet 10a makes contact with the cement 22 and with continuing the movement reaches the final insertion position as shown in FIG. 2.

During insertion, as a result of the radial clearance a, the eyelet 10a can move free play, which allows an adjustment or alignment with a radial component and/or also with an additional axial component (along the direction y). As can be seen from FIG. 2, the cement 22 is displaced in the annular space R between the fastening area on the eyelet side formed by the outer shell surface 25 and the inner shell surface 18, rising in the direction opposite to the direction y, and then finally hardens. Until the hardening is completed, the parallel pin 13 is left in its holding and adjusting position seen in FIG. 1 and removed only after the cement has hardened.

Figure 3:
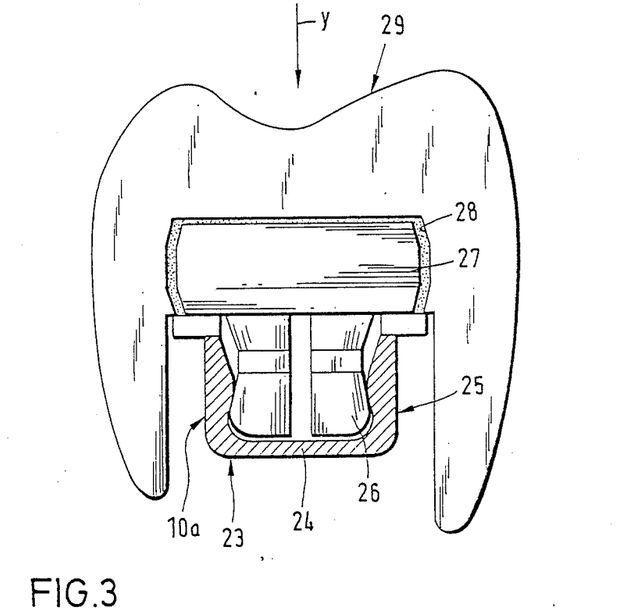
FIG. 3 is a sectional view which shows the insertion of pot-shaped female eyelet in the course of a repair process.

The repair process in the mouth of the patient according to FIG. 3 differs from the illustrations in FIG. 1 and 2 in that the eyelet 10a is already engaged in a well defined position with the male anchor 26 (complementary retention component), whose shank 27 is cemented in a receiving hollow 28 in the prosthesis. By lowering the removable prosthesis part 29 in direction y, the insertion position of the eyelet 10a according to FIG. 2 is finally reached, analogously to the representations of FIG. 1 and 2. Thus, in the representation of FIG. 3, the removable dental prosthesis 29 acts like the parallel pin 13 shown in FIG. 1.

Figure 4:
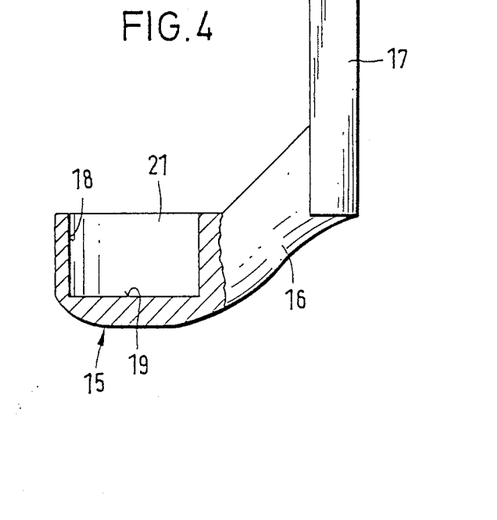
FIGS. 4 and 5 are sectional views of two different embodiments of metal holding parts, each of which has showing an extracoronal holding recess.
Figure 5:
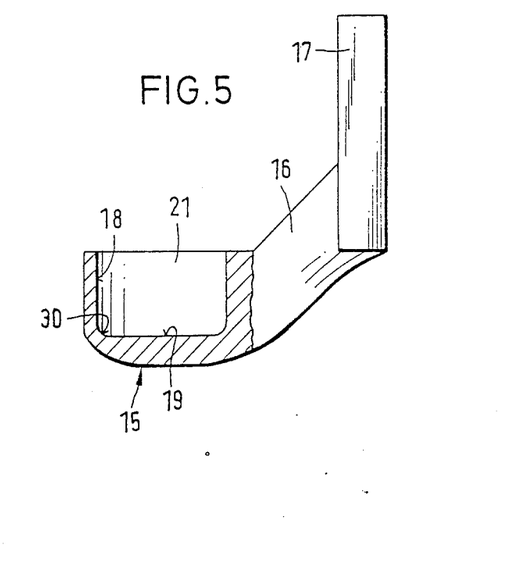

In FIGS. 4 and 5, various embodiments of holding recesses 21 are shown. These have the inner shell surface of a right circular cylinder. Generally, the outer shell surfaces of the retention parts (see FIGS. 11–14) can have contour which is geometrically similar to the respective contour of the inner shell surface 18 (FIGS. 4 and 5), whereby in any case the adjustment-and movement distances a (see FIGS. 2) are insured. However the retention parts generally (FIG. 11–14) can have various outer shell surfaces. Suitably, the outer shell surface 25 of each retention part, here the eyelet 10a, is the surface of a straight circular cylinder. The outer bottom surface 23 and outer shell surface 25 are connected to each other over a convexly curved circular annular surface 36.

It should be pointed out that the circular cylindrical recesses 21 (see FIG. 1–10) already mentioned in FIG. 1–3 are particularly advantageous, since they are very easy to make and also since the retention part, here the eyelet 10a is to be held with a purely axial component withdrawal which is opposite the direction y. The recess 21 of FIG. 5 also differs from the recess 21 of FIG. 4 in that the circular-cylindrical inner bottom surface 19 is joins to the inner shell surface 18 via a concavely curved annular surface 30.

For the sake of clarity, it may also be mentioned that the holders made of a synethetic material which burns without leaving residues, not shown here, are identical in shape with the holders 15 shown in FIGS. 1–5.

Figure 6:
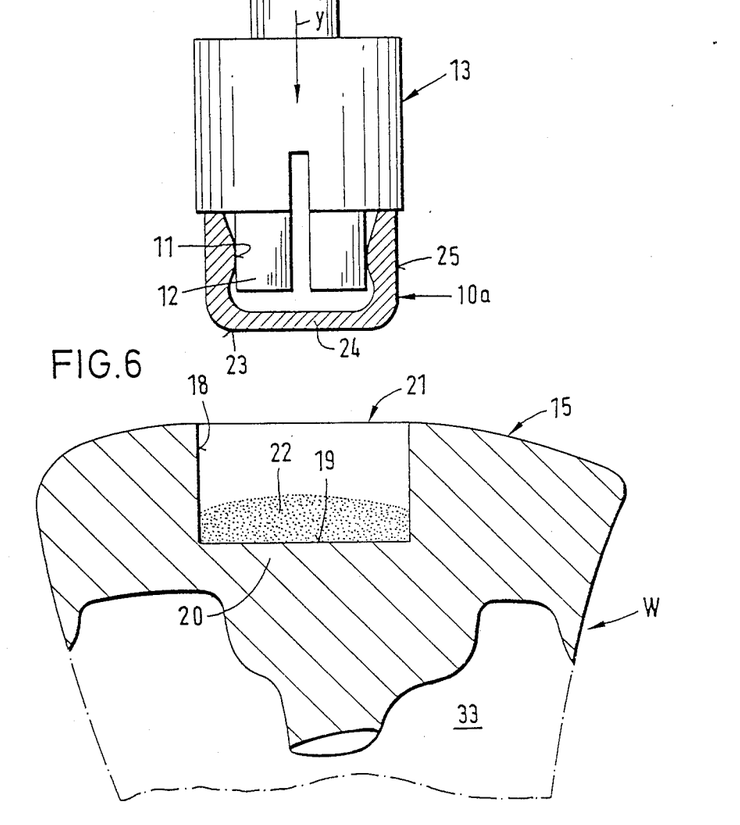
FIG. 6, analogous to FIG. 1, FIG. 7 analogous to FIG. 2, FIG. 8 analogous to FIG. 3, show the method for the insertion of a pot-shaped eyelet in connection respectively with an intracoronal arrangement., i.e. root-cap arrangement.

The description of FIG. 1 can be analogously and to a very large extent applied to FIG. 6 which uses the same reference numerals. But, as a difference from FIG. 1, FIG. 6 shows an intracoronal, axial arrangement, wherein W is a root cap made of metal, 15 indicates the metal holding part and 21 represents the pot-shaped hollow (recess) and its bottom area. The root or its model is indicated at 33.

Figure 7:
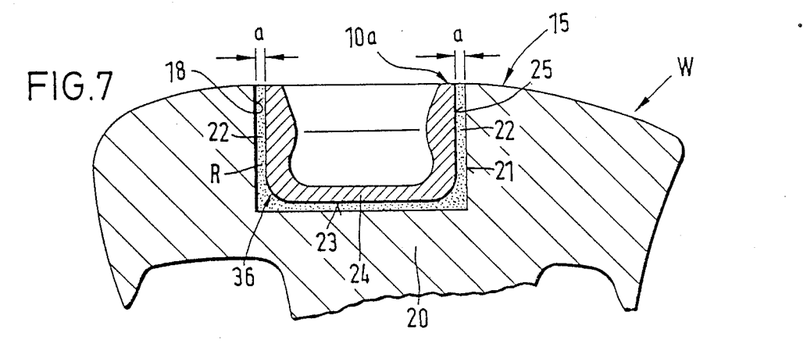

FIG. 7 again is analogous to FIG. 2 and the applicable description showing the completed root-cap arrangement. In this way FIGS. 6 and 7 illustrate the method of insertion of a retention part, here an eyelet-like female part 10a, in the course of producing a new root cap.

Figure 8:
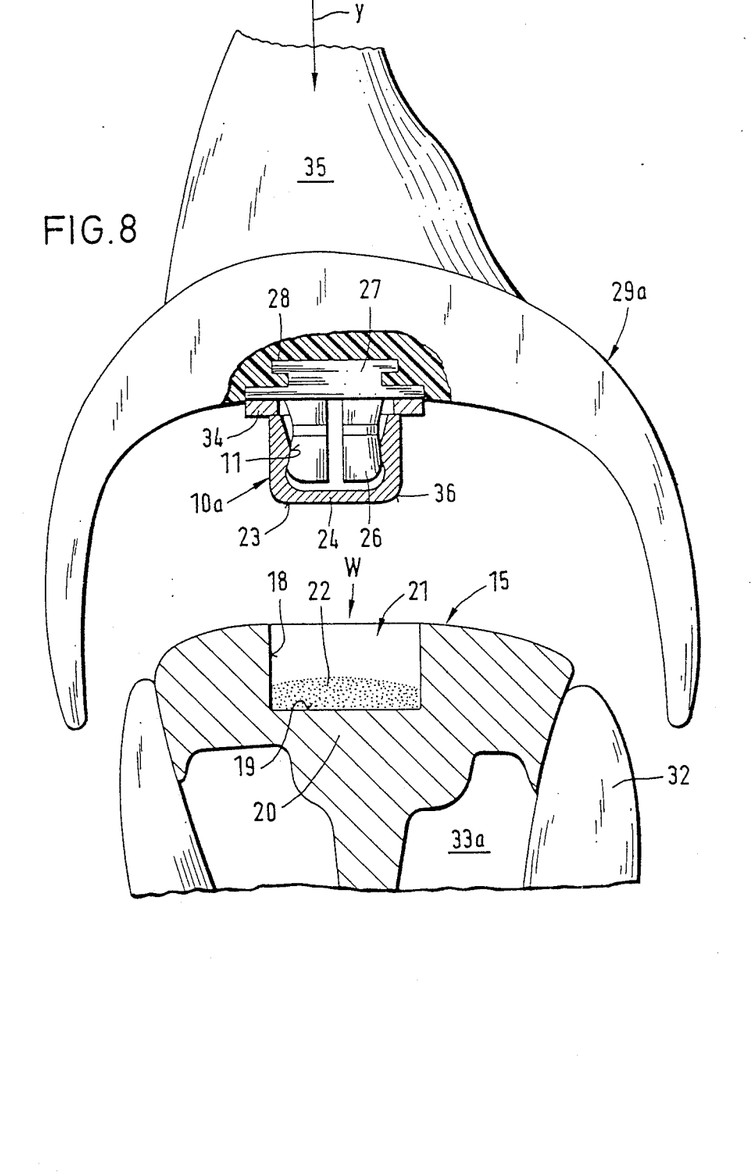

FIG. 8 shows analogously to FIG. 3 and the applicable description the insertion of the retention part (e.g. eyelet-like female part 10a) in the course of a repair process of a root-cap arrangement in the mouth of a patient. Here the root 33a is flanked by the gum 32 and receives removable prosthesis 20 made of synthetic material with artificial tooth 35. To an inner side of the prosthesis 29 at 28 the undercut to whose inner side at 28 the undercut retention area 27 of the anchor 26 is cast at 34.

In the embodiment of FIGS. 9 to 14, various retention parts are shown at 10a, 10b, 10c and 10d.

Figure 9:
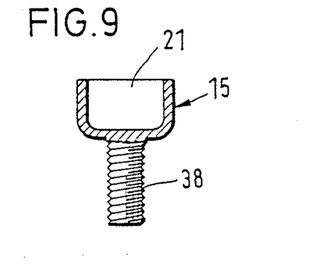
FIG. 9 is a longitudinally sectioned view of an implant-holding part.

FIG. 9 shows a screw with external thread 38, to be inserted in an implant which is not shown in the drawing, and whose head forms the metal holding part 15 with the recess 21.

Figure 10:
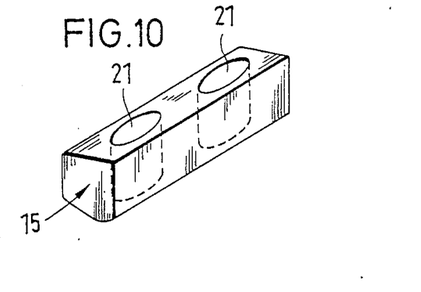
FIG. 10 is a schematic perspective view of a bridge-like holding part.
Figure 11:
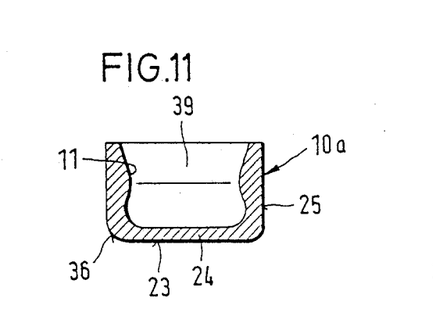
FIG. 11 is an axial section through a pot-shaped threaded part.

FIG. 10 shows schematically a bridge-like component 15 with two recesses 21, made of an synthetic material burning without residue or of a dental material.

FIG. 11 shows again separately the pot-shaped female part 10a, previously shown in FIG. 1, 3 and 6–8. The retention inner shell surface of the eyelet 10a is seen at 11 and the entire undercut retention hollow is represented at 39.

Figure 12:
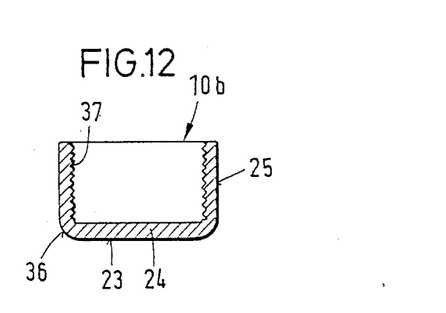

FIG. 12 shows a pot-shaped bushing 10b with internal threading 37 for receiving the external threading of a pin (not shown) of a male anchor part 26.

Figure 13:
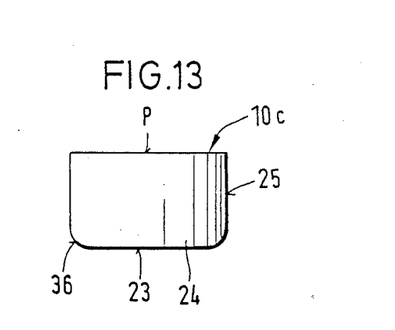
FIG. 13 is a frontal view of a magnet.
Figure 14:
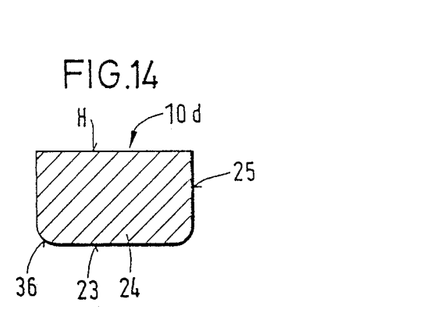
FIG. 14 is an axial section through a ferromagnetic body.

FIG. 13 shows a magnet 10c with a pole surface P in a frontal view and FIG. 14 shows a ferromagnetic body 10d, which can be cemented in the hollow 21, when there is another magnet instead of the magnet 10c. The magnetic surface H of the ferromagnetic body 10d is provided for adhesion to the pole surface P of a magnet 10c.

It has also to be mentioned that, as a rule, all retention parts 10a, 10b, 10c, 10d shown in FIG. 11 to 14 can be cemented with any one of the recesses 21 shown in FIG. 1–10, in the manner proposed by the invention.

Inner shell surfaces 18 and outer shell surfaces 25 of the recesses 18 and the retention parts 10a, 10b, 10c, 10d are always smoothly circularly cylindrical and optionally may be shot-blasted. An axial contour (e.g. a groove) which has not been shown could be worked into 18 or 25, if an additional insurance against torsion about the axis y is required. All retention parts 10a, 10b, 10c, 10d are plunger-like displacement bodies, through which the cement 22, which flowable, is evenly distributed to rise in reverse in the annular space R, without the possibility of the inner retention surface 11 being inadvertently impaired by the cement 22.

I claim:

1. A dental coupling assembly, comprising:
   a holding member having a body anchorable in a mouth and formed with an undercut-free recess opening at a face of said body, said recess being bounded by a right-circularly cylindrical internal wall directly adjoining a circular bottom wall of said recess, said bottom wall continuously spanning across a bottom of said recess, said right-circularly cylindrical wall being peripherally continuous and extending straightly over substantially a full depth of said recess from a junction with said bottom wall to said face;
   a retention member connectable to a dental prosthesis and formed with a plug on one side of said retention member, said plug being received in said recess and having a right-circularly cylindrical peripherally continuous external wall extending straightly from an end of said plug to a level of said face and juxtaposed with said internal wall across an all-around cylindrical gap, said plug having a circular continuous end wall spanning continuously across said end, forming a junction with said external wall and spaced from said bottom wall across a circular gap communicating with said cylindrical gap;
   a mass of adhesive displaced by said plug to fill said gaps and settable to bond said members together while filling said gaps; and
   means for securing a dental prosthesis to an opposite side of said retention member.

2. The dental coupling assembly defined in claim 1 wherein said means for securing a dental prosthesis to said opposite side of said retention member includes an undercut hollow space formed in said opposite side of said retention member so that said retention member has a pot shape, and a male part anchored to said prosthesis and resiliently received in said undercut hollow space to form a snap coupling therewith.

3. The dental coupling assembly defined in claim 2 wherein at least one of said junctions is rounded in cross section.

4. The dental coupling assembly defined in claim 3 wherein the junction of said holding member is a rounded concave junction in cross section.

5. The dental coupling assembly defined in claim 3 wherein the junction of said retention member is a rounded convex junction in cross section.

6. The dental coupling assembly defined in claim 1 wherein at least one of said junctions is rounded in cross section.

7. The dental coupling assembly defined in claim 6 wherein the junction of said holding member is a rounded concave junction in cross section.

8. The dental coupling assembly defined in claim 6 wherein the junction of said retention member is a rounded convex junction in cross section.

9. The dental coupling assembly defined in claim 1 wherein said means for securing a dental prosthesis to said opposite side of said retention member includes an internal screw thread formed on a wall of a bore in said opposite side of said retention member.

10. The dental coupling assembly defined in claim 1 wherein said means for securing a dental prosthesis to said opposite side of said retention member includes a face on said opposite side of said retention member adapted to abut an anchor part anchored in said prosthesis, one of said anchor part and retention member being a permanent magnet, the other of said anchor part and retention member being composed of a ferromagnetic material.

* * * * *